US009989754B2

(12) United States Patent
Anhut et al.

(10) Patent No.: US 9,989,754 B2
(45) Date of Patent: Jun. 5, 2018

(54) LIGHT SCANNING MICROSCOPE WITH SPECTRAL DETECTION

(71) Applicant: Carl Zeiss Microscopy GmbH, Jena (DE)

(72) Inventors: Tiemo Anhut, Jena (DE); Daniel Schwedt, Weimar (DE); Ralf Wolleschensky, Jena (DE); Lars-Christian Wittig, Jena (DE); Ulrich Preiβer, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 561 days.

(21) Appl. No.: 14/383,628

(22) PCT Filed: Feb. 28, 2013

(86) PCT No.: PCT/EP2013/054075
§ 371 (c)(1),
(2) Date: Sep. 8, 2014

(87) PCT Pub. No.: WO2013/131808
PCT Pub. Date: Sep. 12, 2013

(65) Prior Publication Data
US 2015/0145981 A1    May 28, 2015

(30) Foreign Application Priority Data
Mar. 9, 2012    (DE) .................. 10 2012 203 736

(51) Int. Cl.
*G02B 26/02*    (2006.01)
*G02B 21/00*    (2006.01)
(Continued)

(52) U.S. Cl.
CPC ......... *G02B 26/02* (2013.01); *G01N 21/6458* (2013.01); *G02B 21/008* (2013.01);
(Continued)

(58) Field of Classification Search
CPC .. G02B 26/02; G02B 21/008; G02B 21/0064; G02B 21/0032; G02B 21/0076; G02B 2207/113; G01N 21/6458; H04N 5/23296
See application file for complete search history.

(56) References Cited

U.S. PATENT DOCUMENTS 4,615,621 A * 10/1986 Allen .................... G03F 9/7069
                                                 356/399
5,192,980 A *  3/1993 Dixon ...................... G01J 3/30
                                                 250/458.1

(Continued)

FOREIGN PATENT DOCUMENTS

DE    100 33 180    5/2002
DE    103 50 918    4/2005
(Continued)

OTHER PUBLICATIONS

Hell et al. (Space-multiplexed multifocal nonlinear microscopy—© 2001 The Royal Microscopical Society, Journal of Microscopy, 202, 457-463), ("Hell").*
(Continued)

*Primary Examiner* — Sath V Perungavoor
*Assistant Examiner* — Philip Dang
(74) *Attorney, Agent, or Firm* — Haug Partners LLP

(57) ABSTRACT

A light scanning microscope with an illumination module switchable between an illumination with m number of spots and an illumination with n number of spots, a deflecting unit which moves the m or n spots in a predetermined sample region, and a detector module for confocal and spectrally resolved detection of the sample radiation. The detector module has a confocal diaphragm unit, a splitting unit which is arranged downstream of the confocal diaphragm unit, a detector, and an imaging unit which images the partial beams on the detector in a spatially separated manner. The confocal diaphragm unit is switchable between a confocal
(Continued)

diaphragm with exactly m apertures for m-spot illumination and a confocal diaphragm with n apertures for n-spot illumination. The splitting unit has a first beam path for m-spot illumination and a second beam path for n-spot illumination. The splitting unit is switchable between the two beam paths.

17 Claims, 6 Drawing Sheets

(51) Int. Cl.
*G01N 21/64* (2006.01)
*H04N 5/232* (2006.01)

(52) U.S. Cl.
CPC ..... *G02B 21/0032* (2013.01); *G02B 21/0064* (2013.01); *G02B 21/0076* (2013.01); *H04N 5/23296* (2013.01); *G02B 2207/113* (2013.01)

(56) References Cited

U.S. PATENT DOCUMENTS

| | | | | |
|---|---|---|---|---|
| 5,491,550 A * | 2/1996 | Dabbs | ................... | G01B 9/0207 250/227.27 |
| 5,537,247 A | 7/1996 | Xiao | | |
| 5,587,832 A * | 12/1996 | Krause | ................ | G02B 21/004 250/216 |
| 6,028,306 A | 2/2000 | Hayashi | | |
| 6,128,077 A * | 10/2000 | Jovin | ................ | G01J 3/10 356/310 |
| 6,185,030 B1 * | 2/2001 | Overbeck | .............. | G02B 21/34 250/586 |
| 6,201,639 B1 * | 3/2001 | Overbeck | .............. | B01L 3/0241 359/225.1 |
| 6,657,216 B1 * | 12/2003 | Poris | ................ | G01B 11/0608 250/216 |
| 7,212,338 B2 | 5/2007 | Weyh | ................ | G02B 21/002 356/300 |
| 7,312,919 B2 * | 12/2007 | Overbeck | .............. | G02B 21/34 359/368 |
| 7,324,200 B2 * | 1/2008 | Shimada | ............ | G01N 21/6456 250/458.1 |
| 7,369,305 B2 * | 5/2008 | Wolleschensky | .... | G02B 15/173 359/380 |
| 7,488,931 B2 * | 2/2009 | Wolleschensky | .... | G02B 15/173 250/201.3 |
| 7,561,326 B2 * | 7/2009 | Funk | ................ | G01J 3/02 359/368 |
| 7,599,591 B2 * | 10/2009 | Andersen | ............. | A61B 3/0008 385/115 |
| 7,633,053 B2 * | 12/2009 | Wolleschensky | .... | G02B 21/002 250/201.3 |
| 7,872,799 B2 * | 1/2011 | Wolleschensky | ..... | G01J 3/1256 359/386 |
| 2001/0053019 A1 * | 12/2001 | Zavislan | ............ | G02B 21/0032 359/370 |
| 2003/0230710 A1 * | 12/2003 | Wolleschensky | ...... | G02B 26/06 250/234 |
| 2005/0094261 A1 | 5/2005 | Hell et al. | | |
| 2005/0111082 A1 * | 5/2005 | Karin | ................. | G02B 21/0032 359/358 |
| 2006/0012870 A1 * | 1/2006 | Engelmann | ........ | G01N 21/6458 359/385 |
| 2006/0187516 A1 | 8/2006 | Lauer | | |
| 2007/0057211 A1 | 3/2007 | Bahlman et al. | | |
| 2008/0006615 A1 * | 1/2008 | Rosario | .................. | B23K 15/08 219/121.68 |
| 2008/0292177 A1 * | 11/2008 | Sheets | ................... | G03F 9/7084 382/151 |

FOREIGN PATENT DOCUMENTS

| | | |
|---|---|---|
| DE | 10 2006 045 839 | 4/2008 |
| EP | 1 970 744 | 9/2008 |
| JP | 2003/140051 | 5/2003 |
| WO | WO 2008/037346 | 4/2008 |

OTHER PUBLICATIONS

Zipfel et al. ("Nonlinear magic: multiphoton microscopy in the biosciences"—Nature Biotechnology vol. 21 No. 11 Nov. 2003), ("Zipfel").*
Notification of Transmittal of the Translation of International Preliminary Report on Patentability dated Sep. 9, 2014.
International Search Report for Application No. PCT/EP2013/054075 dated Jul. 4, 2013.
German Search Report for Application No. 10 2012 203 736.5 dated Jul. 18, 2012.
S.W. Hell et al., "*Space-multiplexed multifocal nonlinear microscopy*", *Journal of Microscopy*, vol. 202, Pt 3, Jun. 2001, pp. 457-463.
Nanguang Chen et al., "*Focal modulation microscopy*", Nov. 10, 2008/vol. 16, No. 23/Optics Express 18764-18769.
Warren R Zipfel et al., "*Nonlinear magic: multiphoton microscopy in the biosciences*", Nature Biotechnology, vol. 21, No. 11, Nov. 2003, pp. 1369-1377.

* cited by examiner

LIGHT SCANNING MICROSCOPE WITH SPECTRAL DETECTION

The present application claims priority from PCT Patent Application No. PCT/EP2013/054075 filed on Feb. 28, 2013, which claims priority from German Patent Application No. DE 10 2012 203 736.5 filed on Mar. 9, 2012, the disclosures of which are incorporated herein by reference in their entirety.

FIELD OF THE INVENTION

It is noted that citation or identification of any document in this application is not an admission that such document is available as prior art to the present invention.

Light scanning microscopes with spectral detection are used, e.g., for fluorescence microscopy with biological samples so that the latter may be examined with a very high spatial resolution. Biological samples of this kind are frequently labeled by one or more fluorescent dyes (or fluorescent proteins) and are, for example, living cells to be examined for dynamic effects. Therefore, spectral sensitivity on the one hand and the rate of image capture at the lowest possible excitation power on the other hand are important for minimizing the phototoxicity of the experiment. Thus whether it is, for example, a spectrally high-resolution imaging or a faster imaging with limited spectral resolution that is required is a matter of the individual sample and the aim of the study.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph), such that applicant(s) reserve the right to disclaim, and hereby disclose a disclaimer of, any previously described product, method of making the product, or process of using the product.

SUMMARY OF THE INVENTION

On this basis, therefore, the object of the invention is to further develop a light scanning microscope for spectral detection in such a way that it can easily be adapted to various required parameters for the examination of a sample.

This object is met by a light scanning microscope with an illumination module for exciting sample radiation in a predetermined region of a sample, which illumination module can be switched between an illumination with m spots, where m is an integer that is greater than or equal to 1, and an illumination with n spots, where n is an integer and is greater than m, a deflecting unit which moves the m or n spots in the predetermined region, and a detector module for confocal and spectrally resolved detection of the sample radiation, wherein the detector module has a confocal diaphragm unit, a splitting unit for spectral spreading of the sample radiation into partial beams, which splitting unit is arranged downstream of the confocal diaphragm unit, a detector, and an imaging unit which images the partial beams on the detector in a spatially separated manner, wherein the confocal diaphragm unit can be switched between a confocal diaphragm with exactly m apertures for the sample radiation during illumination with m spots and a confocal diaphragm with n apertures for the sample radiation during illumination with n spots, and the splitting unit has, from the confocal diaphragm unit to the imaging unit, a first beam path for the sample radiation during illumination with m spots and a second beam path for the sample radiation during illumination with n spots, and the splitting unit can be switched between the two beam paths.

By providing the confocal diaphragm unit in combination with the splitting unit having the switchable beam paths, confocal and spectrally resolved detection can be provided in an optimal manner for each of the possible illuminations.

The confocal diaphragm unit can have a confocal diaphragm which is switchable between m apertures and n apertures. Alternatively, the confocal diaphragm unit can have a first confocal diaphragm with exactly m apertures and a second confocal diaphragm with n apertures, wherein the switching between the first confocal diaphragm and the second confocal diaphragm is caused by switching the beam path. In particular, the confocal diaphragm with n apertures can have exactly n apertures.

As a result of the ability to switch between m apertures and n apertures, there are k=2 different possible operating modes of the light scanning microscope. Expressed in another way, there are k different parallelizing steps. Of course, k can also be greater than two. In that case, the confocal diaphragm can be switched between k different states with k different apertures. Further, the illumination module can provide the corresponding quantity of illumination spots preferably for all k states.

On the one hand, the apertures of the confocal diaphragm(s) can actually be openings or transparent areas in a diaphragm. On the other hand, it is possible to produce the apertures of the confocal diaphragm(s) through a reflective portion such that only light impinging on the reflective portion reaches the splitting unit. The reflecting portion is a kind of "inverted" aperture. Although the word "aperture" is generally used hereinafter, it is to be understood both as an opening or transparent area in a diaphragm in the conventional sense and also as a reflective portion which acts as a confocal diaphragm in the described manner.

The m and/or n apertures are, for example, adjustable in size in a mutually dependent manner and in particular can be adjusted in such a way that all n diaphragm apertures or all m diaphragm apertures are always identical in size. It is also possible that the m diaphragm apertures and the n diaphragm apertures are adjustable in size independently from one another.

In particular, the confocal diaphragm or the confocal diaphragms is or are formed in such a way that the m apertures or n apertures are adjustable in size in a continuous manner.

Further, the confocal diaphragm unit can be formed in such a way that the quantity of m apertures or n apertures can be changed.

It is further preferred that m=1. In this case, the confocal diaphragm having exactly one aperture can also be called a monofocal diaphragm. If n is greater than 1, the diaphragm can be called a multifocal diaphragm. The confocal diaphragm with n apertures is always a multifocal diaphragm because it has at least two apertures.

The m diaphragm apertures or n diaphragm apertures of the multifocal diaphragm can lie on a line. Other arrangements are also possible. For example, the m diaphragm apertures or n diaphragm apertures can be arranged in a two-dimensional matrix A diaphragm aperture of the multifocal diaphragm can lie on the principal beam axis during monofocal detection when the sample is illuminated by one spot.

The confocal diaphragm unit can have two diaphragm elements which are displaceable relative to one another in order to change the m or n aperture(s) of the confocal diaphragm and/or switch between the two confocal diaphragms. Flexure bearings, piezo actuators and/or servomotors can be used to move the two diaphragm elements. Other actuating means are also possible for carrying out the displacement.

In case of detection with the confocal diaphragm with exactly m apertures, the detector can be a detector with a plurality of linearly arranged detector elements or a detector with a plurality of detector elements arranged two-dimensionally. This is also true for the detector in case of detection with the confocal diaphragm with n apertures. In particular, the same detector can be used in case of detection with the confocal diaphragm with m apertures and in case of detection with the confocal diaphragm with n apertures. In particular, the detector can be a detection unit, a multi-element detector, a detector having detector elements arranged in one dimension or two dimensions, a multianode photomultiplier or, e.g., a one-dimensional or two-dimensional avalanche photodiode array.

Further, in particular the same imaging unit can image the partial beams on the detector regardless of whether they originate from the first beam path or from the second beam path. Accordingly, in this case there is a common beam path for the partial beams from the imaging unit to the detector.

To this end, e.g., a switchable or movable mirror (for example, a concave mirror) can be provided which deflects in each instance from the first beam path or from the second beam path to the common beam path. Further, a movable or switchable mirror can be provided which is arranged downstream of the confocal diaphragm unit and switches between the first beam path and second beam path. Instead of mirrors for switching the beam paths, other suitable optical elements such as prisms, for example, can also be provided. If possible, these elements can also be utilized for spectral spreading.

In the light scanning microscope according to the invention, a separate unit for spectral spreading of the sample radiation can be arranged in each of the two beam paths.

The separate unit can have, in each instance, a dispersive prism, a reflection grating, a transmission grating and/or one or more filters. It is also possible to carry out a pre-dispersion in one direction through at least one filter and/or at least one prism and to carry out a further dispersion in another direction through a grating.

In this way, it is possible to disperse the sample radiation during the illumination with a plurality of spots (e.g., n spots) in such a way that spectrum and locus are orthogonal to one another, wherein an imaging is then preferably carried out on a two-dimensional detector.

It is also possible to split the sample radiation during illumination with a plurality of spots (e.g., n spots) in such a way that spectrum and locus of the spots are split in the same direction, wherein the different spots are arranged such that they are spectrally split next to one another. In this case, the detector can be formed, e.g., as a linear sensor.

The splitting can be carried out by means of a dispersive prism, a reflection grating, a transmission grating and/or through one or more filters.

In a preferred manner, the spot spacing is adapted beforehand to the detector size by means of magnification optics (e.g., telescope optics). In a plane in which the spots or bundles are spatially separated, an angular magnification can be carried out by means of segmented optics without increasing the optical imaging scale. To this end, a mirror with a plurality of facets in fixed angular relationship to one another can be used, for example. A mirror with a plurality of facets whose angular relationships to one another are adjustable can also be used. The quantity of facets of the segmented mirror is preferably equal to the quantity of spots.

A diaphragm can be positioned in a pupil plane in front of the segmented mirror for blocking light components which are diffracted at the confocal diaphragm.

The segmented optics can be formed as a matrix of microlenses. The microlenses can have a negative refractive power in each instance. The microlenses can be arranged behind the confocal diaphragm or they can be positioned behind the intermediate image of the telescope optics. In particular, the distance can amount to a few millimeters.

Further, the segmented optics can be formed as a waveguide structure, wherein at least one waveguide is associated with each spot or bundle. The inputs of the waveguide structure are preferably positioned in the focal plane of the input lens of the telescope optics. The outputs of the waveguide structure can be positioned in the focal plane of the output line of the telescope optics.

The outputs of the waveguide structure have greater distances from one another than the inputs. The waveguide structure can be selected particularly as bundles of light-conducting fibers.

In particular, the splitting unit in the light scanning microscope according to the invention can have magnification optics and an optics unit for locally increasing the numerical aperture of the partial beams. An optics unit of this type for locally increasing the numerical aperture can be realized, for example, by means of a microlens array in which the individual lenses have a negative refractive power in each instance. The microlens array can be arranged behind the confocal diaphragm or can be positioned behind an intermediate image of the magnification optics. In particular, the distance can amount to a few millimeters. A smaller focus is obtained in the detector plane through the optics unit for locally increasing the numerical aperture and can therefore increase the magnification factor of the magnification optics in an advantageous manner.

The optics unit for locally increasing the numerical aperture is preferably arranged in front of the magnification optics so that with respect to the partial beams the numerical aperture is initially increased and the optical magnification is then carried out by mean of the magnification optics.

Further, in addition or alternatively, the splitting unit can have magnification optics with first partial optics and second partial optics and a waveguide structure, wherein the first partial optics have a first focal plane between the two partial optics, and the second partial optics has a second focal plane which is at a distance from the first focal plane and which is located between the two partial optics, and the waveguide structure has a waveguide for each of the m apertures or n apertures of the confocal diaphragm unit, wherein the inputs of the waveguides are located in the first focal plane and the outputs of the waveguides are located in the second focal plane, and wherein the distance between the outputs of the waveguides is greater than the distance between the inputs of the waveguides. Therefore, the waveguides displace the point images of the spots from the first focal plane to the second focal plane.

The magnification optics can be produced, for example, starting from telescope optics with an intermediate image plane. The telescope optics have two partial optics whose distance from one another is increased so that the focal planes are spread apart. The distance between the two spread-apart focal planes is then bridged by the waveguides, wherein the latter generate the above-described displacement of the point images relative to one another. The waveguides can be realized as glass fiber bundles or as a waveguide structure, for example.

The spectral splitting of the sample radiation during illumination with a plurality of spots (e.g., n spots) such that spectrum and locus of the spots are split in the same direction, wherein the different spots are arranged such that they are spectrally split next to one another, can also be achieved in that a plurality of filters generate a plurality of spectral channels which are imaged on different sensor elements because of the filter orientation. In particular, adjustable edge filters can be used. With this type of splitting, the spectral channels corresponding to the filters are next to one another, and the spots lie next to one another in each spectral channel.

In particular, in case of illumination with n spots, the splitting unit can split spectrum and locus of the spots in the same direction such that spot portions of the same wavelength lie directly next to one another.

The plurality of spectral channels exit the arrangement of filters in bundles which combine the spot-dependent partial bundles. These bundles are preferably imaged on the detector in such a way that they are spaced apart from one another by at least one sensor element. Every bundle and, therefore, every spectral channel can be limited in bandwidth via a further transmission filter. The transmission filter can be an edge filter or a bandpass filter, for example.

The bundles and, therefore, every spectral channel can preferably be imaged on the detector in such a way that they are spaced apart from one another by at least one sensor element.

In addition to the imaging of the spectral channels on a linear detector, an imaging on a two-dimensional detector is also possible.

The deflecting unit in the light scanning microscope according to the invention can supply the sample radiation to the detector module as descanned sample radiation. By this is meant in particular that the excited sample radiation which runs opposite to the direction of the illumination radiation and impinges on the deflecting unit is present as quiescent sample radiation downstream of the deflecting unit.

The light scanning microscope can be constructed in particular as a laser scanning microscope. In this case, laser radiation is used to illuminate the sample. However, it is also possible to use radiation other than laser radiation to illuminate the sample.

Further, a confocal diaphragm unit can also be provided in the illumination module to realize the switchable illumination with m spots or n spots. In particular, the confocal diaphragm unit of the illumination module can be formed in the same way as the confocal diaphragm unit of the detector module.

Further, the light scanning microscope can have additional modules known to the person skilled in the art which are needed for the operation of the light scanning microscope.

Further, there is provided a light scanning microscopy method in which the illumination of a predetermined region of a sample for exciting sample radiation can be switched between an illumination with m spots, where m is an integer and is greater than or equal to 1, and an illumination with n spots, where n is an integer and is greater than m, the m or n spots are moved for illumination in the predetermined region, and the sample radiation is detected confocally and in a spectrally resolved manner by a detector module, wherein the detector module has a confocal diaphragm unit, a splitting unit for spectral spreading of the sample radiation into partial beams, which splitting unit is arranged downstream of the confocal diaphragm unit, a detector and an imaging unit which images the partial beams on the detector in a spatially separated manner, wherein the confocal diaphragm unit can be switched between a confocal diaphragm with exactly m apertures for the sample radiation during illumination with m spots and a confocal diaphragm with n apertures for the sample radiation during illumination with n spots, and the splitting unit is switched between a first beam path for the sample radiation during illumination with m spots, which first beam path runs from the confocal diaphragm unit to the imaging unit, and a second beam path for the sample radiation during illumination with n spots, which second beam path runs from the confocal diaphragm unit to the imaging unit.

The light scanning microscopy method according to the invention can be further developed in the same way as the light scanning microscope according to the invention. In particular, it can have the method steps described in connection with the light scanning microscope according to the invention and further development thereof.

It will be appreciated that the features which have been mentioned above and which will be described hereinafter can be used not only in the combinations indicated, but also in other combinations or individually without departing from the scope of the present invention.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
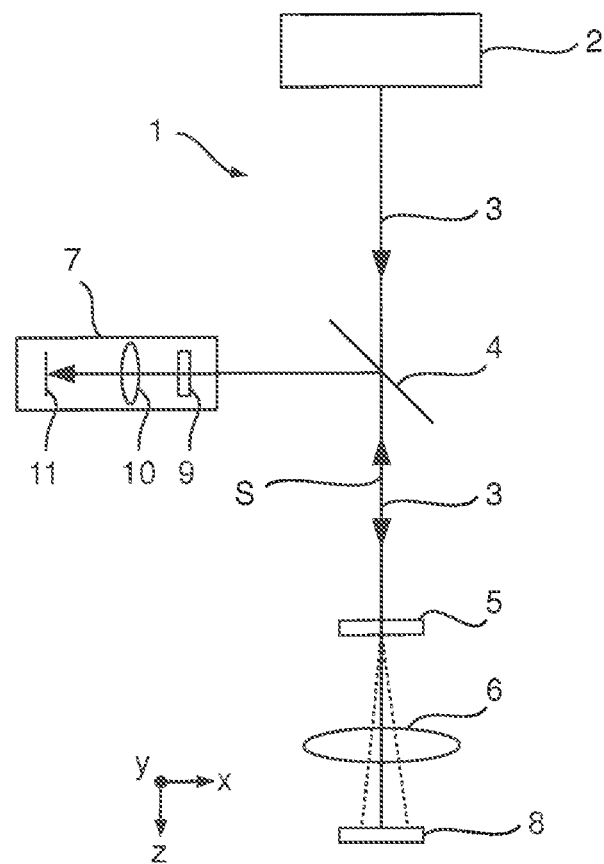
FIG. 1 shows a schematic view of a first embodiment form of the light scanning microscope according to the invention.

In the embodiment form shown in FIG. 1, the light scanning microscope 1 according to the invention, which can be formed particularly as a laser scanning microscope, comprises an illumination module 2 which emits illumination radiation 3, a main splitter 4 which passes at least a portion of the illumination radiation 3, a deflecting unit 5, an objective 6 and a detector module 7.

The illumination module 2 is designed such that it is switchable between a single spot illumination and a multi-spot illumination. As is indicated schematically by the dashed lines, the single spot and multi-spots of illumination is/are moved in a predetermined region of a sample 8 to be examined by the deflecting unit 5 which has, e.g., one or two galvanometer mirrors. Expressed differently, the single spot or multispots execute a scanning movement in the predetermined region. In this way, the predetermined region is scanned by the single spot or multispots. For this reason the deflecting unit 5 is often referred to as scanner.

The single spot is, for example, a laser beam which is spot-focused in the predetermined region of the sample 8 and which is moved by the deflecting unit 5 in at least one direction (X direction and/or Y direction) transverse to the propagation direction (Z direction) of the laser beam so as to achieve the scanning movement. The multispot is, for example, a plurality of laser beams which are spot-focused in the predetermined region and which are spaced apart in the predetermined region and moved by the deflecting unit 5 simultaneously in X direction and/or Y direction to generate the scanning movement. Of course, the single spot and multispot are not limited to spot-focusing in the predetermined region of the sample 8. Other types of focusing such as a line focus, for example, are also possible. However, spot-focusing is assumed hereinafter.

Sample radiation S (e.g., fluorescent radiation) is generated in the sample 8 by the single spot illumination or multispot illumination. This sample radiation S runs opposite to the illumination radiation 3 via the objective 6 to the deflecting unit 5, is descanned by the latter (downstream of the deflecting unit 5, the sample radiation S is present as quiescent radiation which is no longer moved transverse to the propagation direction), and is then deflected to the detector module 7 at the main splitter 4.

The detector module 7 carries out a confocal, spectrally resolved detection of the sample radiation S and, for this purpose, has a confocal diaphragm unit 9, imaging optics 10 downstream of the latter, and a detector 11 as will be described in more detail in the following. Of course, the light scanning microscope 1 can also be designed in such a way that the illumination module 2 uses the main splitter 4 in reflection and the sample radiation S is guided to the detector module 7 in transmission via the main splitter 4. First, the illumination module will be described in more detail with reference to FIG. 2.

The illumination module includes a laser 12, a switching unit 13 downstream of the laser 12, a beam splitting unit 14, a first optical polarizing beam splitter 15 and illumination module optics 16.

The laser radiation emitted by the laser 12 is guided to the switching unit 13 which can be switched between two light paths. To this end, it has a rotatably arranged half-wave plate 17 with which the polarization state of the laser radiation can be changed. Depending on the selected polarization state, the laser radiation is guided from a second optical polarizing beam splitter 18 either to the beam splitting unit 14 or to a deflecting mirror 19 of the switching unit 13.

Figure 2:
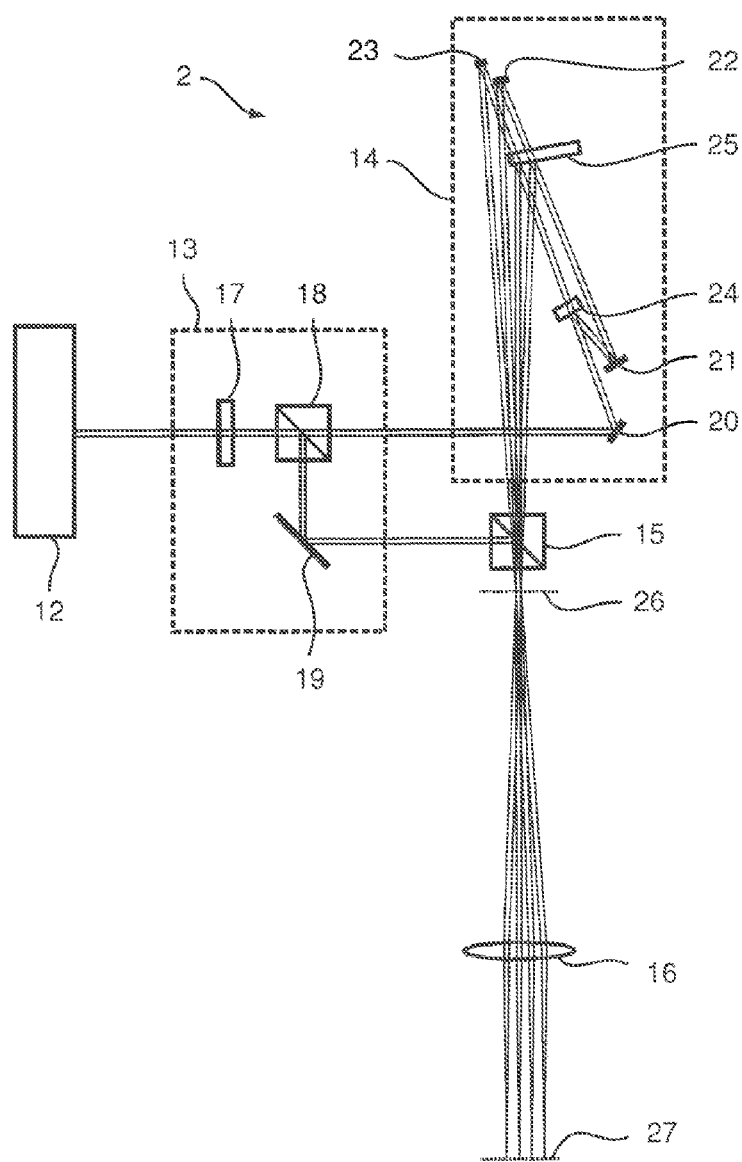
FIG. 2 shows a schematic depiction of the illumination module 2 of the light scanning microscope of FIG. 1.

FIG. 2 shows in greater detail the case in which the radiation is guided along the first light path of the switching unit 13 into the beam splitting unit 14 which comprises four highly reflective mirrors 20 to 23 and two 50:50 splitters 24 and 25 which have a splitter coating on one side and an antireflective coating on the other side. Mirrors 20 to 23 are preferably dielectric mirrors with a reflectivity of greater than 99.5% so as to minimize beam path-dependent losses. The background to this is that the partial beams impinge on a different quantity of mirror surfaces in the beam splitting unit 14 and, therefore, mirrors 20 to 23 preferably have a particularly high reflectivity so that the losses do not accumulate inhomogeneously. Mirrors 20 to 23 and splitters 24 and 25 are arranged in the beam splitting unit 14 in such a way that four beams extend in a plane and adjacent beams form a constant angle with one another in each instance. The beams accordingly intersect in a pupil plane 26 which is located behind the first beam splitter 15 and which is imaged on the deflecting unit 5 (or scanner) and in the pupil of the objective 6 by the illumination module optics 16. Accordingly, four laser spots arrayed in a line which are spaced apart from one another at constant intervals and have approximately the same brightness lie in the intermediate image plane 27 generated by the illumination module optics 16.

Mirrors 20-23 and splitters 24 and 25 in the beam splitting unit 14 can also be arranged in such a way that the partial beams run apart at constant angles in a common plane. In this case, the rearwardly elongated beams intersect in a virtual pupil which must then be imaged on the scanner 5 and in the pupil of the objective 6. This configuration is particularly compact.

Splitting into four partial beams is used only by way of example. Naturally, it is also possible to split into a greater number of partial beams. In that case, it would merely be necessary to provide a corresponding quantity of splitters 24, 25 and, mirrors 20-23. It is also possible to block one or more partial beams so that a correspondingly suitable quantity of partial beams is generated as illumination radiation.

Alternatively, with suitable positioning of the half-wave plate 17, the radiation of the laser 12 can be guided along the second light path of the switching unit 13 via the deflecting mirror 19 directly to the first optical polarizing beam splitter 15 rather than into the beam splitting unit 14. An individual focused spot is then present in the intermediate image plane 27.

Therefore, in the described embodiment form with the illumination module 2 with single spot illumination, an individual laser spot can be generated which is guided over the sample 8 by means of the scanner 5. In multispot illumination, four laser spots which are arrayed next to one another in a line are generated and are again guided over the sample 8 by the scanner 5.

The laser radiation of the laser 12 can be guided to the switching unit 13 via a free beam path or via a light-conducting fiber. The switching unit 13 can be implemented as a separate device, a subassembly which is integrated in the beam path of the light scanning microscope 1, or as part of the laser 12 (for example, as fiber switch or integrated optical switch).

In the embodiment example described here, the beam splitting and beam combining are carried out by means of optical polarizing beam splitters 15, 18, and the light paths and, therefore, the mode of operation of the illumination module 2 are selected by means of the half-wave plate 17. However, other arrangements are also possible. For example, the switching of the beam paths by means of switchable mirrors (e.g., folding mirrors, galvanometer mirrors or MOEMS (micro-opto-electro mechanical systems). Different working principles such as switchable mirrors for switching the beam paths and optical polarizing beam splitters for beam combining can also be used for beam splitting in the switching unit 13 on the one hand and for beam combining on the other hand.

Figure 3:
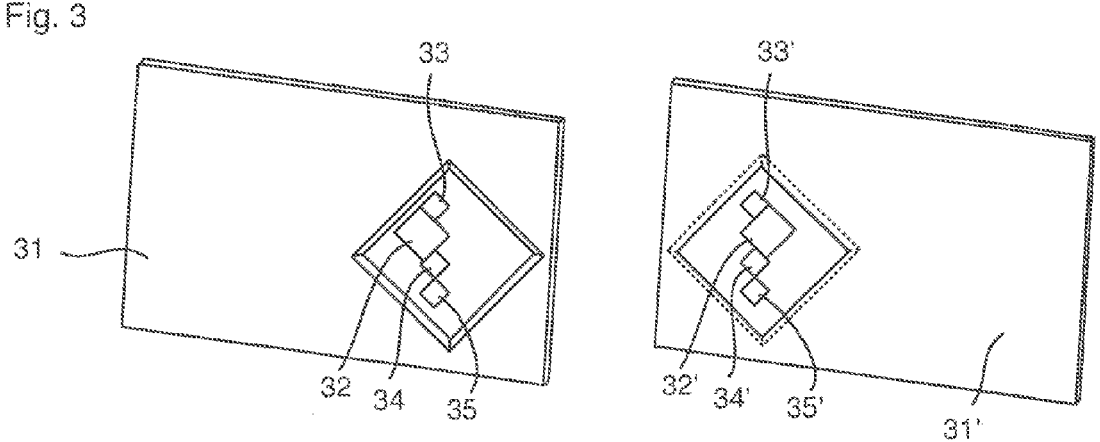
FIG. 3 shows a schematic depiction of two diaphragm elements of the confocal diaphragm of the confocal diaphragm unit 9 from FIG. 1.

Accordingly, it is possible by means of this switchable illumination module 2 to switch between a single spot illumination and a multispot illumination (in this case with four spots). In order to carry out confocal detection for single spot illumination as well as multispot illumination, the confocal diaphragm unit 9 in the embodiment form described here has a first diaphragm element 31 and a second diaphragm element 31' which are shown schematically in FIG. 3. The diaphragm elements 31, 31' have a rectangular main aperture 32, 32', respectively, and rectangular auxiliary apertures 33, 33', 34, 34' and 35, 35', respectively, adjoining the rectangular main aperture 32, 32'.

Figure 4A:
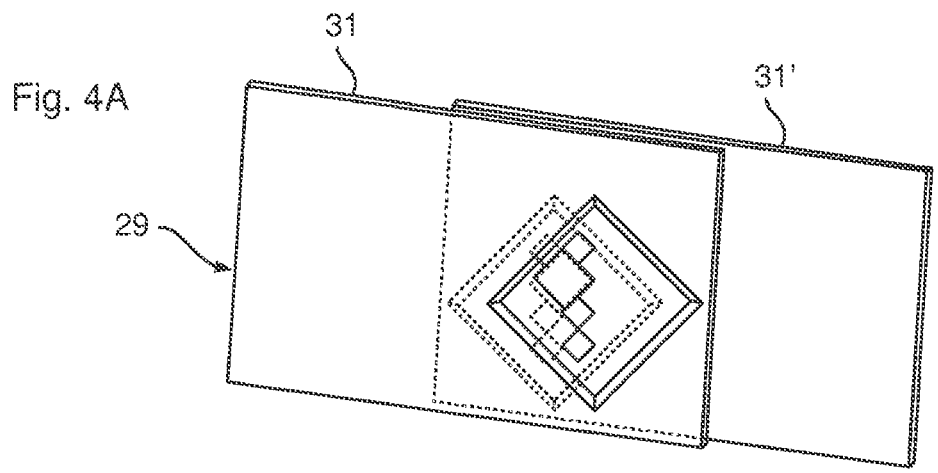
FIGS. 4A-4C show different positions of the two diaphragm elements relative to one another in order to change the size of an individual pinhole.
Figure 4B:
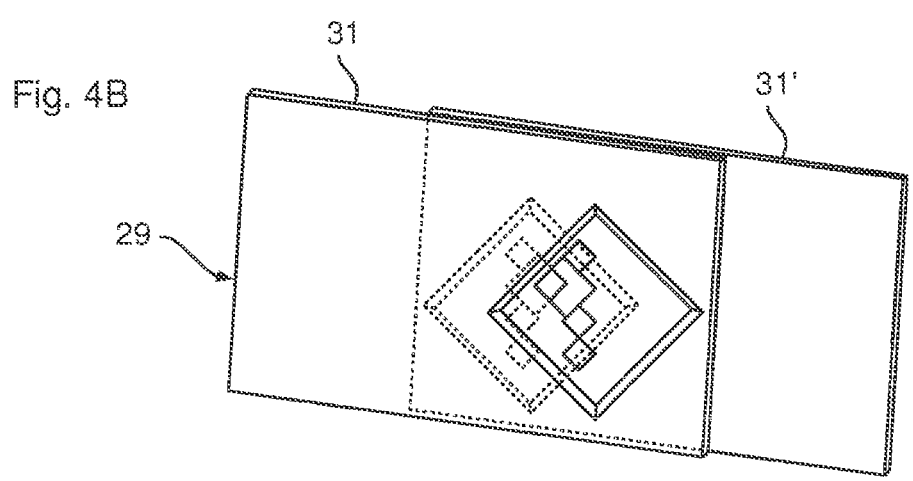
Figure 4C:
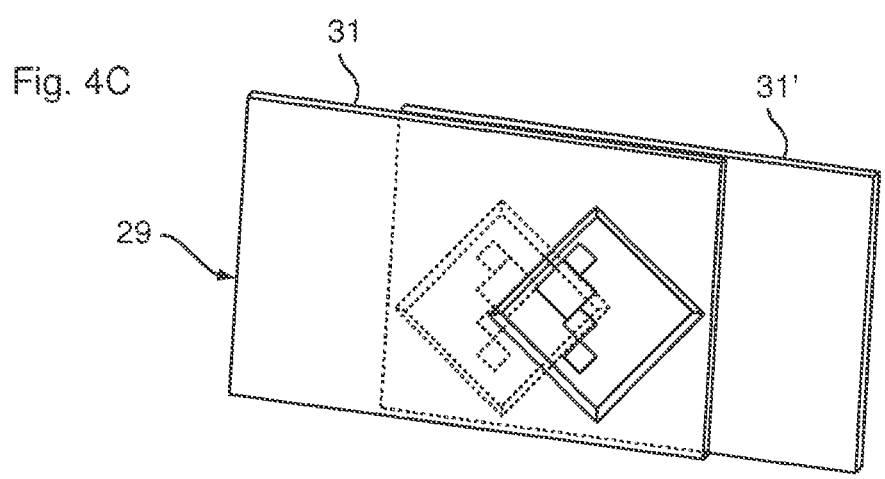

The diaphragm elements 31, 31' are displaceable relative to one another as is shown schematically in FIGS. 4A to 4C and form an adjustable confocal diaphragm unit 9. In FIG. 4A, the two main apertures 32 and 32' are arranged so as to be coextensive one behind the other so that a pinhole with an edge length of about 400 μm is provided.

In the position of the two diaphragm elements 31 and 31' shown in FIG. 4B, the two main apertures 32 and 32' only partially overlap, so that the pinhole provided in this case has an edge length of about 200 μm.

FIG. 4C shows the case in which the main apertures 32 and 32' do not overlap at all so that the pinhole is closed. As can be seen from FIGS. 4A-4C, a pinhole which can be adjusted in size quasi-continuously can be provided for single spot illumination with the two diaphragm elements 31 and 31'. In this way, the pinhole for single spot illumination can be optimally adapted for the respective measuring job. A good spatial and spectral resolution can be achieved with a small pinhole. A large pinhole can be used when the optical sectioning is already realized on the excitation side, for example, as in multiphoton microscopy. The optimal pinhole diameter in focus modulation microscopy can also be greater than in confocal microscopy, wherein, as a rule, the pinhole diameter is adjustable depending upon illumination and application.

Figure 5A:
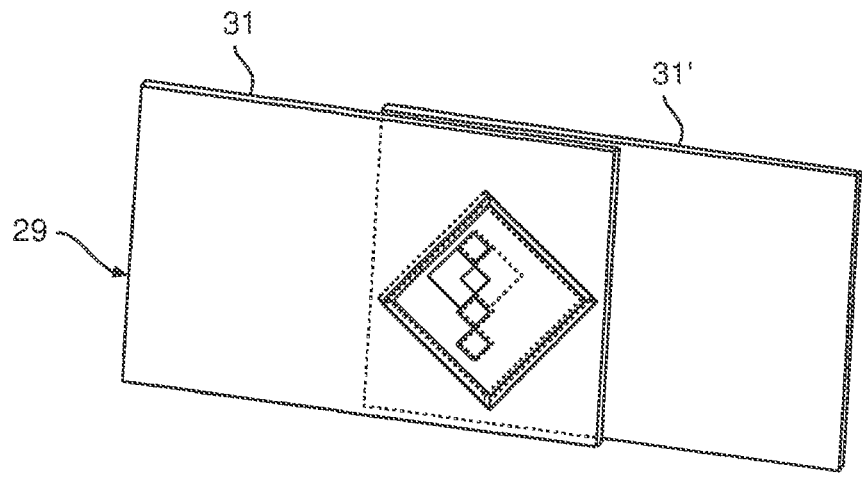
FIGS. 5A-5C show different positions of the two diaphragm elements relative to one another in order to change the size of four pinholes.
Figure 5B:
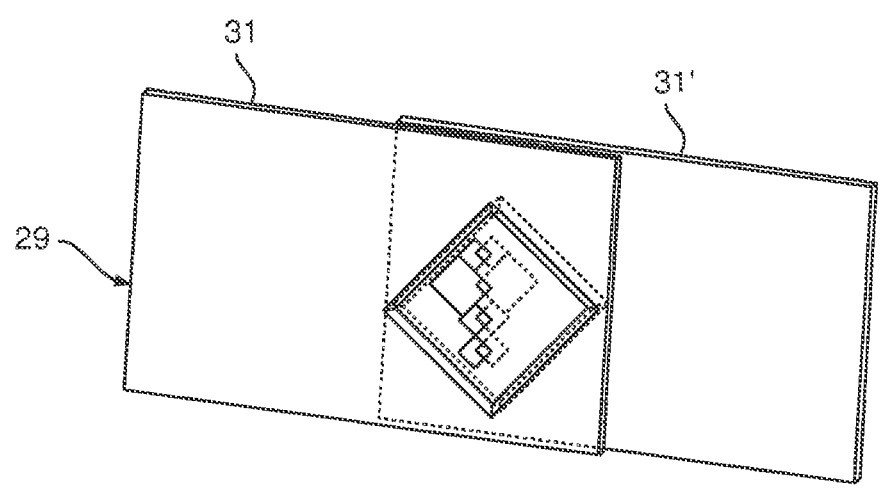
Figure 5C:
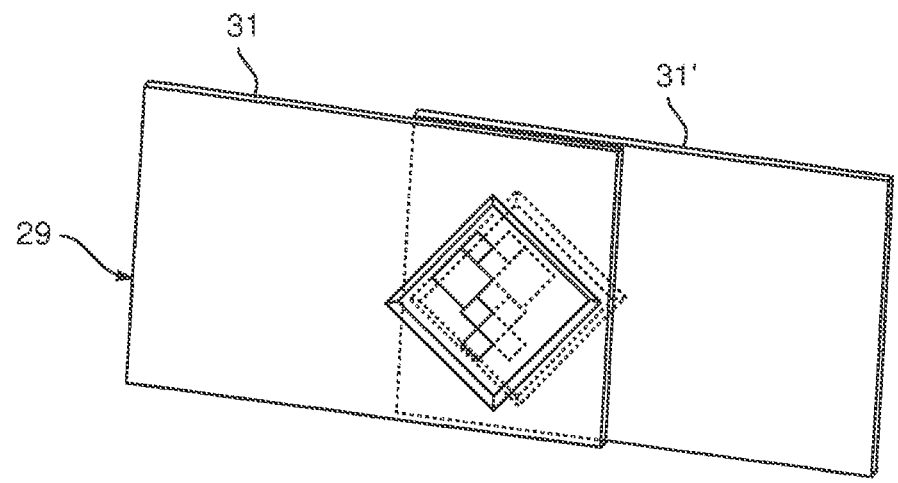

FIGS. 5A-5C show positions of the two diaphragm elements 31, 31' for multispot illumination. In the depiction in FIG. 5A, four pinholes with an edge length of about 240 μm are provided. In the position of the two diaphragm elements 31 and 31' shown in FIG. 5B, the four pinholes have an edge length of approximately 120 μm. In the position shown in FIG. 5C, all four pinholes are closed. Here also, it is possible again to change the size of the four pinholes in a quasi-continuous manner, wherein the individual pinholes are preferably the same size.

Alternatively, it is possible not only to displace the two diaphragm elements 31 and 31' transverse to the arrangement of the apertures 32-35, 32'-35' as is shown in FIGS. 4A-4C and 5A-5C, but also in direction of the arrangement of apertures 32-35, 32'-35' and, therefore, from the bottom to the top in the views according to FIGS. 4A-4C and FIGS. 5A-5C. In this way, it is possible, e.g., to switch the confocal diaphragm 6 between a confocal diaphragm with four pinholes and a confocal diaphragm with three pinholes and, further, to change the size of the three pinholes or four pinholes.

In the embodiment form described here, the four spots or regions to be detected confocally lie on a line, one of the four spots or regions corresponding to the main optical beam used for monofocal microscopy. However, this is only an advantageous embodiment which is not compulsory. Other arrangements are also possible. For example, the four pinholes (or generally the n pinholes, where n is an integer greater than 1) can be arranged in a matrix (i.e., not along a line). In so doing, one pinhole can correspond to the pinhole for the single spot illumination. Alternatively, a separate pinhole can be provided for single spot illumination.

The two diaphragm elements 31 and 31' can be arranged directly in a conventional detection module instead of a single-channel confocal diaphragm. In this connection, pinhole optics which are arranged between the main splitter 4 on the one hand and the two diaphragm elements 31 and 31' on the other hand and which are a component part of the confocal diaphragm unit 9 should transmit the entire light field with high optical quality. The pinhole optics can also be configured as zoom optics. In this way, different pinhole sizes can be adjusted from a combination of optical size and mechanical aperture of the diaphragm elements 31, 31'. Further, a system in which the identical array of pinhole diaphragms can be used with variable spot spacing in sample 8 can be realized in this way. A change in the spot spacing in the other direction is then compensated again via a corresponding zoom adjustment, or zoom optics are placed directly in front of the scanner 5. In an advantageous manner, the diaphragm diameter is changed at the same time so that the confocal characteristics are retained.

The two diaphragm elements 31 and 31' can be moved by means of one or more suitable actuators, e.g., a flexure bearing, a piezo actuator, a servomotor or stepper motor with linear guide or by other means.

Figure 6:
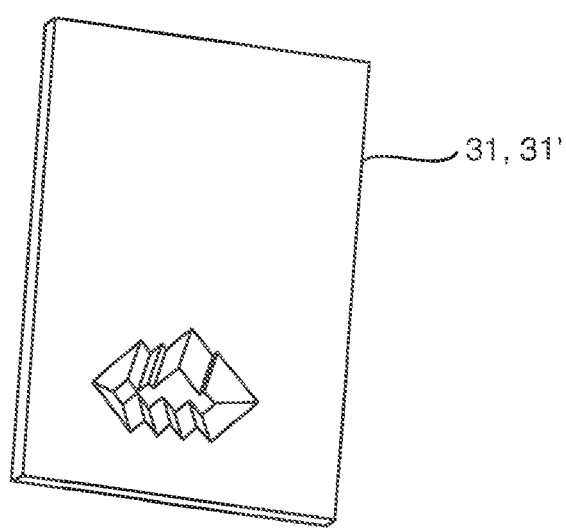
FIG. 6 shows a view of a further diaphragm element.

FIG. 6 shows a further diaphragm element 31, 31' by way of example. By means of a corresponding arrangement of two elements of this kind relative to one another and displacement as was described in connection with FIGS. 4A-4C and 5A-5C, it is possible to switch between single spot operation and multispot operation, and the size of the pinhole or pinholes can be adjusted simultaneously. The different embodiments of the diaphragm elements 31, 31' described with reference to FIGS. 3 and 6 result from different etching technologies or from the use of different wafers in the production of the silicon-based diaphragms. Of course, the diaphragms can be produced with similar geometries from other materials, e.g., such as by laser cutting of thinned metal foil.

If the single spot and/or multispots is/are provided as line-focused laser beam or laser beams, the pinhole shapes of the confocal diaphragm can, of course, be adapted in a corresponding manner.

It is also possible to realize the herein-described principle of switching between a single spot diaphragm and a multi-spot diaphragm by means of switchable elements. To this end, reflecting MEMS (micro-electro mechanical systems) can also be realized, for example. In this case, the pinholes are realized by reflective elements. Accordingly, no actual aperture, but rather a very small reflecting surface acting as pinhole is provided, since only light impinging on this small surface or small surfaces is reflected and is analyzed in the detector 11.

Figure 7:
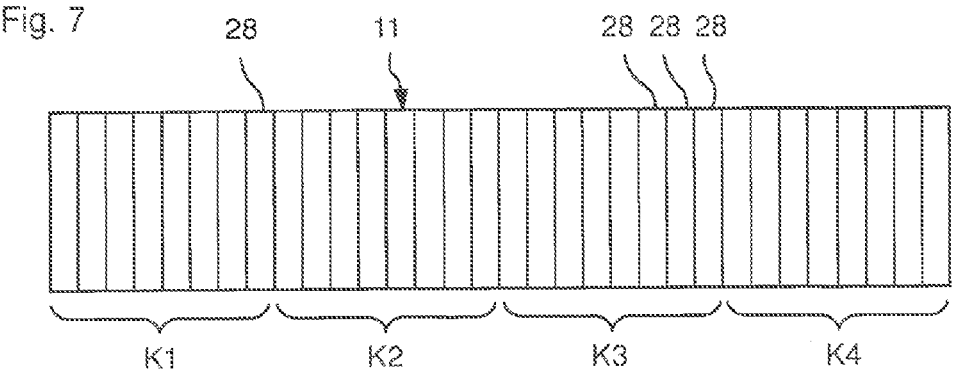
FIG. 7 shows a schematic depiction of the detector 11.

As is shown schematically in FIG. 7, the detector 11 is configured in this case as a sensor line with thirty-two elements 28 (e.g., a multianode photomultiplier) and is utilized in such a way that with single spot illumination the confocally detected sample radiation S is spectrally spread out on all thirty-two elements 28 of the detector 11. In case of multispot illumination with four spots, the spectrally detected four spots are spectrally spread out and arranged adjacent to one another such that one of the four detected spots is spectrally spread out in each of the regions K1 to K4. Accordingly, up to eight elements 28 of the detector 11 are available for one of the four channels K1-K4 for spectral detection.

Figure 8:
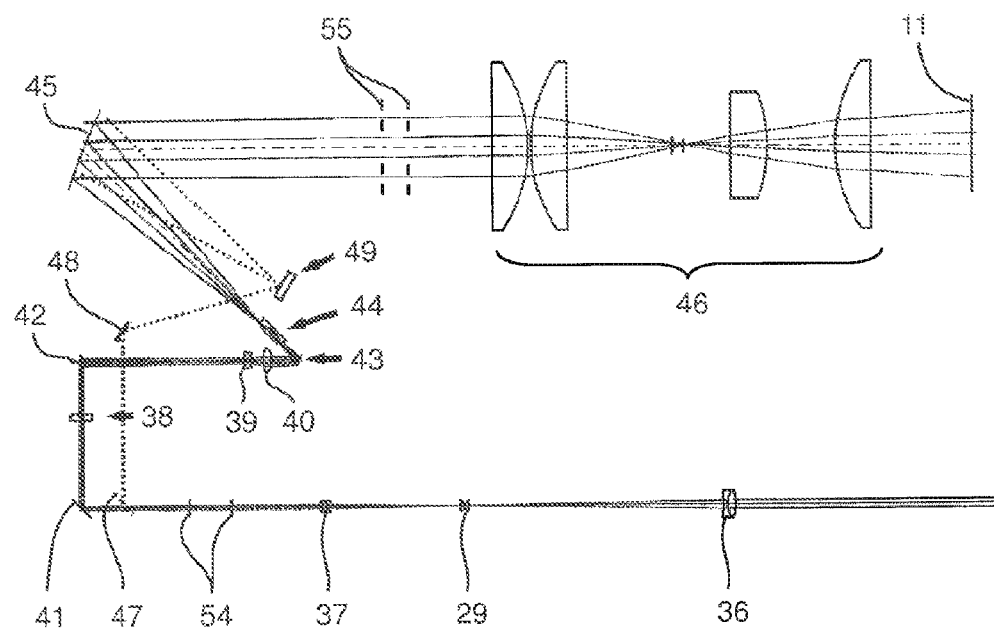
FIG. 8 shows a schematic depiction of the detector module 7 from FIG. 1.

In order to carry out this detection, the beam path in the detector module 7 is switchable. FIG. 8 shows two beam paths, wherein the beam path for multispot illumination is indicated by solid lines and the beam path for single spot illumination is indicated chiefly by dashed lines.

The detector module 7 contains the above-described confocal diaphragm 29, including pinhole optics 36, a collimator 37 downstream of the confocal diaphragm 29, three lenses 38, 39 and 40 which form telescope optics, two deflecting mirrors 41, 42 for beam path folding, a segmented mirror 43, a direct-vision prism 44, a concave mirror 45, detection optics 46 and detector 11.

In the embodiment form described here, the imaging of the pinholes for multispot illumination on the detector 11 requires 18× magnification so that the corresponding spot signals for a determined wavelength impinge on an associated element 28 of the sensor 11 in each instance. However, in case of purely optical magnification such as can be carried out by means of a telescope, for example, the imaging PSF (point spread function=point response) on the detector 11 is scaled with the same factor. As a result of this, the required spectral edge steepness is no longer produced in some cases. To counter this, the imaging is carried out in multiple steps, wherein a first step is, e.g., a typical telescopic magnification, and a second step produces the angular distance between the n bundles (in this case four bundles) in a purely geometrical manner by deflecting these bundles independently from one another. An axial position in which the bundles are spatially separated is suitable for this purpose. In this way, the angles between the n bundles are changed, but not the imaging quality (e.g., PSF size, spectral edge steepness, etc.) on the detector 11.

Figure 9:
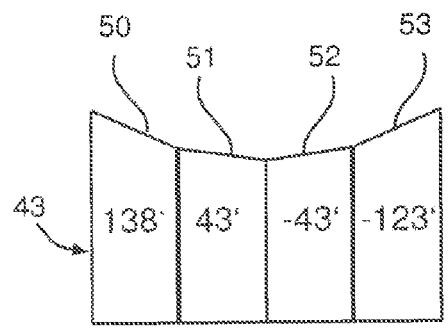
FIG. 9 shows an enlarged view of the segmented mirror 43 from FIG. 8.

The first step of telescopic magnification is carried out in this case by means of the three lenses 38 to 40, wherein the focal length of lenses 38 is 88 mm and the focal lengths of lenses 39 and 40 is 30.7 mm. Accordingly, the bundles impinge on the segmented mirror 43 with a diameter of 0.5 mm and with a spacing of 1.0 mm as is shown in an enlarged view in FIG. 9. The segmented mirror 43 has four reflective segments or facets 50, 51, 52, 53 having an angle of inclination of 138', 43', −43' and −123'. The individual beam bundles reflected by the facets 50-53 run through the direct-vision prism 44 which can be configured, e.g., as an Amici prism, so that the free angular distance between the bundles is filled with spectral information and these bundles are imaged on the detector due to the concave mirror 45 and detection optics 46. Thus a spectral spreading is carried out by means of prism 44 so that the spectral information for each of the four channels K1-K4 impinges on eight elements 28 of the detector 11, wherein the four channels K1-K4 are arranged adjacent to one another so that all thirty-two elements 28 of the detector 11 are used for detection.

A deflecting mirror 47 which can be positioned in the beam path between collimator 37 and deflecting mirror 41 is provided for single spot illumination. This position is shown in dashes in FIG. 8. The detected radiation is accordingly deflected on a further deflecting mirror 48 and from the latter to a grating 49 which carries out the desired spectral splitting. A deflection is carried out from the grating 49 in direction of the concave mirror 45 so that an imaging can be carried out in turn on the detector 11 by means of detection optics 46.

The concave mirror 45 can be adjustable with respect to its viewing direction in order to switch between the multi-focal beam path and the monofocal beam path.

There are also other possible means for geometric angular magnification apart from the segmented mirror 43. For example, a microlens array can be arranged a few millimeters behind the confocal diaphragm 29, a microlens with negative refractive power being associated with each pinhole. In this way, the numerical aperture can be increased by spots so that a smaller spot profile results in the detector plane. The axial position of the microlens array is determined by a compromise between the least possible blooming of the lens aperture (smallest possible distance from the confocal diaphragm) and the effect of the increase in the numerical aperture (greater distance, beam waist is drawn behind the pinhole).

A rearrangement of the spots in an intermediate image inside a telescope likewise has a purely geometrically enlarging effect. In this case, the telescope (lenses 38 to 40) affords magnifying imaging of the confocal diaphragm on the detector 11, wherein the distance of the first lens 38 from lens 39 is increased so that the focal plane of lens 38 (first partial optics) no longer coincides with the focal plane of lenses 39, 40 (second partial optics). This rearrangement can take place by means of a glass fiber bundle or by means of a waveguide structure. The condition for this consists in that the outputs of the fibers of the glass fiber bundle or of the waveguide structure which lie in the focal plane of the second partial optics are at a greater distance from one another than the inputs of the glass fiber bundles or waveguide structure which lie in the focal plane of the first partial optics.

In the construction shown in FIG. 8, there can be optical crosstalk in the signals of the individual spots due, for example, to blooming of facets 50-53 of the segmented mirror 43. This can be brought about, e.g., by diffraction effect at the pinhole or via long wavelength-shifted spectra of red emitting dyes which then already illuminate the blue channels of the subsequent spots again. The spectrally induced crosstalk can be minimized by inserting a shortpass filter 54 into the beam path or with correspondingly adapted anti-reflection coatings and reflection coatings on the existing optical elements. The crosstalk brought about by facet bloom can be minimized in that a diaphragm 55 which blocks the light components diffracted from the nominal beam path is inserted in a pupil plane of the multifocal beam path in which all beams intersect.

Diffraction-induced crosstalk can also be suppressed by using a waveguide structure in that the acceptance angle for the waveguiding is selected through the choice of waveguide materials such that diffracted light from the adjacent pinhole does not undergo any waveguiding.

In case at least one partial beam is blocked in multispot illumination as was described above as a possible alternative, only the relevant sensor elements 28 can be read out in the simplest case. For example, if a partial beam whose excited sample radiation would be detected in region K4 of the detector 11 is blocked, the sensor elements of region K4 are not read out and/or evaluated.

Figure 10:
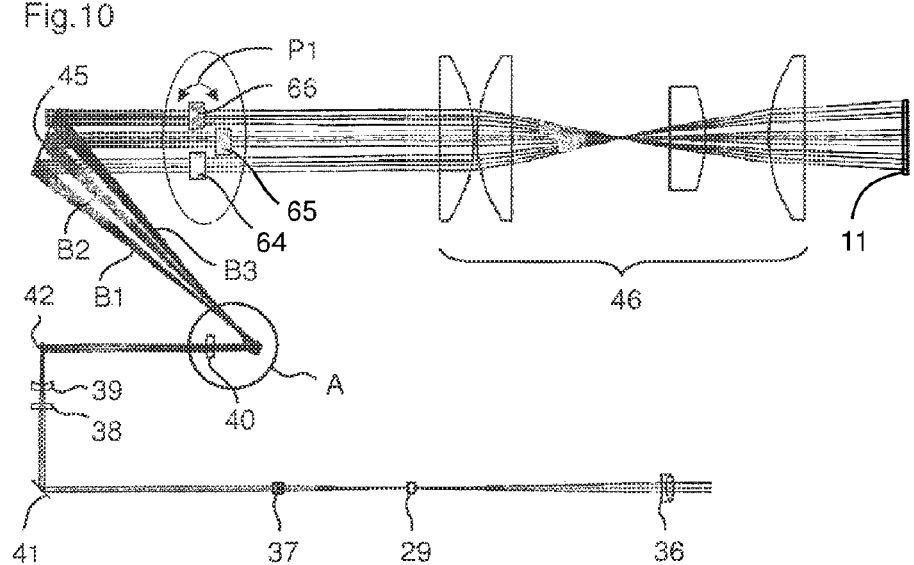
FIG. 10 shows a depiction of a further embodiment form of the detector module 7 from FIG. 1.

FIG. 10 shows a configuration of the detector module 7 in which the splitting into three different spectral channels is carried out by means of filters, wherein at least two are adjustable with respect to their spectral reflection characteristic and transmission characteristic. This can be realized, for example, via edge filters with extending spectral position of the filter edge, which edge filters can be displaced independently from one another. A third filter can be constructed as a stationary element with a constant filter function, possibly also as a broadband mirror, since this need only reflect the spectral emission remainders on the red or blue edge of the spectral region.

Figure 11:
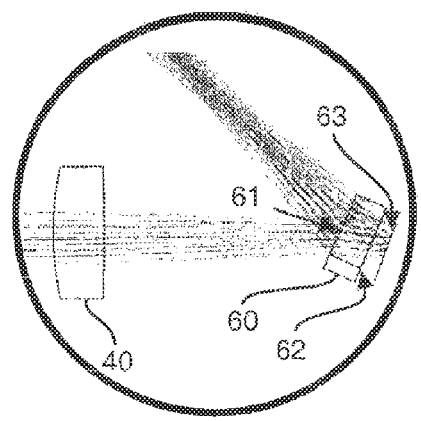
FIG. 11 shows an enlarged view of detail A from FIG. 10.

In the embodiment example shown in FIG. 10, the two adjustable filter functions are realized on a substrate 60, wherein one filter function is on the front side 61 of the substrate 60 and the second filter function is on the back side 62 as can best be seen in FIG. 11 from the enlarged view of detail A from FIG. 10. The filter substrate 60 is provided with a wedge angle so that the two generated spectral images are ultimately imaged on different sensor elements of the detector 11. The filter substrate 60 can be displaceable in two orthogonal directions lateral to the beam axis, for example. The change in the spectral position of the filter edge on the front side 61 changes through displacement of filter 60 in one direction, and the spectral filter edge on the back side 62 of the filter changes when displaced in the direction orthogonal to this direction. The stationary third filter is designated by reference numeral 63 in FIG. 11.

The beam path for the single spot is not shown in FIGS. 10 and 11 but can be configured in the same way as in the embodiment form according to FIG. 7.

Figure 12:
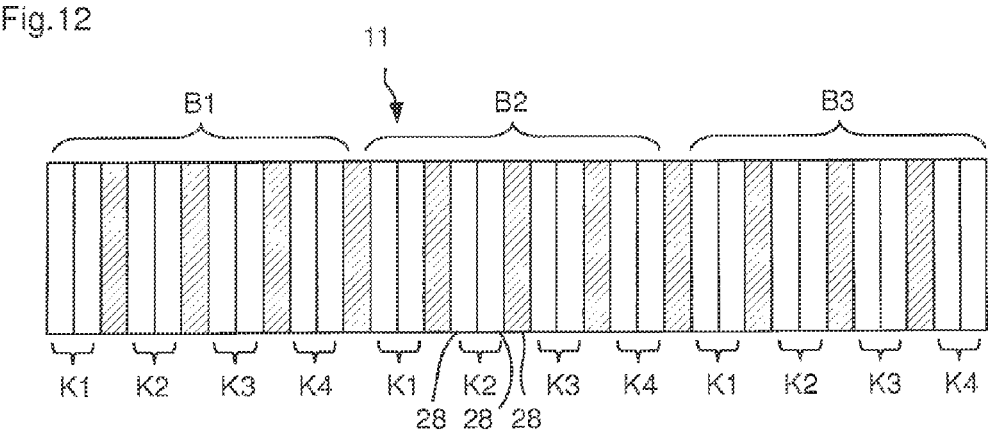
FIG. 12 shows a further view of the detector 11.

The light reflected by the three filter surfaces now exits the filter cascade in three spectral bands B1, B2 and B3 of four bundles each (corresponding to the four pinholes) at different angles such that the downstream optics 45, 46 image the four spots (K1-K4) within a spectral band on the detector 11 with a sensor element safety distance (i.e., this element is not read out under certain circumstances and is shown in shaded portions in FIG. 12). The sample radiation of each pinhole is accordingly divided between the three spectral bands B1-B3 and designated as K1, K2, K3 and K4 in FIG. 12. The distance between the spectral bands B1, B2 and B3 is at least one element (shaded in FIG. 12). Therefore, the detector 11 according to FIG. 12 has thirty-five sensor elements 28. Of course, the respective distance between the spectral bands B1-B3 can be more than one sensor element 28. For example, a distance of at least four to five elements 28 is preferred. In this case, of course, the detector 11 has a corresponding quantity of sensor elements 28. This effectively eliminates optical and electronic crosstalk between the spots and between the spectral channels B1-B3.

Of course, the filter-based embodiment form can also be configured in such a way that, e.g., a 32× multianode photomultiplier 11 can be used as is shown in FIG. 7. When only one sensor element is associated with each spot per spectral band B1-B3, safety clearance can also be provided between the spectral channels: 4×(3 colors)×2 (because of one-element safety distance)=twenty-four sensor elements 28 as minimum pixilation. This has the advantage that a commercial multianode photomultiplier by Hamamatsu (H7260-200) can be used. Of course, the remaining eight sensor elements (32−24=8) can also still be used as safety distance between the utilized sensor elements 28.

Once the bundles of spectral bands B1-B3 are distinctly separated from one another, transmission filters 64, 65, 66 (e.g., one transmission filter 64, 65, 66 per spectral band B1-B3) can be inserted, the filter characteristics of these transmission filters 64, 65, 66 being configured either as edge filter (preferably shortpass filter) or bandpass filter. The transmission filters 64-66 can be arranged, for example, at a position between the concave mirror 45 and the detection optics 46 as is illustrated in FIG. 10. Further, transmission filters 64-66 are arranged so as to be rotatable (indicated by arrow P1) preferably around a substrate edge so that they can be swung completely out of the beam path on the one hand. In this case, they do not interfere with monofocal operation. On the other hand, the spectral position of the red flank of the respective spectral region can be adjusted in this way. The use of VersaChrome filters by Semrock Inc. is particularly advantageous for this purpose because they do not exhibit any division between p-polarization and s-polarization over a very large angular area and the fluorescence for both polarization directions can therefore be detected with uniform sensitivity and in correct bandwidth. A displacement of the channel flanks by 80 to 100 nm can be realized in this way. The bandwidth of this detection channel can accordingly be adjusted in a virtually continuous manner so that autofluorescence can be efficiently blocked, for example.

A further possibility for achieving variability of the filtration is afforded when the light scanning microscope 1 is outfitted primarily with lasers of fixed wavelengths as is the case with a good 90 percent of confocal microscopes for linear fluorescence excitation. Then, combinations of filter edges which are adapted to the combinatorics of every possible combination of lasers can be arranged on the front side 61 and back side 62 resulting in innumerable filter combinations. The filter functions are preferably configured as longpass filters. However, shortpass filters can also be used in an advantageous manner.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A light scanning microscope comprising:
    an illumination module configured to excite sample radiation in a predetermined region of a sample, the illumination module being switchable between an illumination with m spots, where m is an integer that is greater than or equal to 1, and an illumination with n spots, where n is an integer and is greater than m;
    a deflecting unit which moves the m or n spots in the predetermined region; and
    a detector module configured to detect, via confocal and spectrally resolved detection, the sample radiation;

wherein the detector module has:
  a confocal diaphragm unit;
  a splitting unit configured to spectrally spread the sample radiation into partial beams, the splitting unit being arranged downstream of the confocal diaphragm unit;
  a detector; and
  an imaging unit configured to image the partial beams on the detector in a spatially separated manner;
  wherein the confocal diaphragm unit is switchable between a confocal diaphragm with exactly m apertures for the sample radiation during illumination with m spots, and a confocal diaphragm with n apertures for the sample radiation during illumination with n spots;
  wherein the splitting unit has, from the confocal diaphragm unit to the imaging unit, a first beam path for the sample radiation during illumination with m spots, and a second beam path for the sample radiation during illumination with n spots; and
  wherein the splitting unit is switchable between the first and second beam paths.

2. The light scanning microscope according to claim 1; wherein the confocal diaphragm unit has a confocal diaphragm which is switchable between m apertures and n apertures.

3. The light scanning microscope according to claim 1; wherein the confocal diaphragm unit has:
  a first confocal diaphragm with exactly m apertures; and
  a second confocal diaphragm with n apertures; and
  wherein the switching between the first confocal diaphragm and the second confocal diaphragm is caused by switching the beam path.

4. The light scanning microscope according to claim 1; wherein a size of each m aperture and/or a size of each n aperture is switchable between at least a first size and a second size.

5. The light scanning microscope according to claim 1; wherein the same detector is used for detecting the sample radiation during illumination with m and n spots.

6. The light scanning microscope according to claim 1; wherein the sample radiation is split during illumination with n spots in such a way that spectrum and locus are orthogonal to one another.

7. The light scanning microscope according to claim 1; wherein the splitting unit splits spectrum and locus of the spots in a same direction during illumination with n spots such that the different spots are arranged so as to be spectrally split next to one another.

8. The light scanning microscope according to claim 1; wherein the splitting unit splits spectrum and locus of the spots in a same direction during illumination with n spots such that spot portions of the same wavelength lie directly next to one another.

9. The light scanning microscope according to claim 1; wherein the splitting unit has:
  magnification optics; and
  an optics unit configured to increase angles of the partial beams relative to one another without changing the optical imaging scale.

10. The light scanning microscope according to claim 8; wherein the optics unit configured to increase the angles has a segmented optical element.

11. The light scanning microscope according to claim 1; wherein the splitting unit has:
  magnification optics; and
  an optics unit for locally increasing a numerical aperture of the partial beams.

12. The light scanning microscope according to claim 1; wherein the splitting unit has:
  magnification optics comprising:
    first partial optics; and
    second partial optics; and
  a waveguide structure;
  wherein the first partial optics have a first focal plane between the two partial optics;
  wherein the second partial optics have a second focal plane which is at a distance from the first focal plane, and which is located between the two partial optics;
  wherein the waveguide structure has a waveguide for each of the m apertures or n apertures of the confocal diaphragm unit;
  wherein an input of each waveguide is located in the first focal plane, and an output of each waveguide is located in the second focal plane; and
  wherein a distance between the outputs of two of the waveguides is greater than a distance between the inputs of the two of the waveguides.

13. The light scanning microscope according to claim 1; wherein a separate unit configured to spectrally spread the sample radiation is arranged in each of the first and second beam paths of the splitting unit.

14. The light scanning microscope according to claim 1; wherein m=1.

15. The light scanning microscope according to claim 1; wherein the deflecting unit is configured to supply the sample radiation to the detector module as descanned sample radiation.

16. The light scanning microscope according to claim 1; wherein the confocal diaphragm unit is switchable between k confocal diaphragms with k different quantities of apertures, where k is an integer greater than two.

17. A light scanning microscopy method comprising:
illuminating a predetermined region of a sample to excite sample radiation, wherein the illumination is switchable between an illumination with m spots, where m is an integer that is greater than or equal to 1, and an illumination with n spots, where n is an integer and is greater than m;
moving the m or n spots for illumination in the predetermined region; and
detecting the sample radiation confocally and in a spectrally resolved manner by a detector module;
wherein the detector module has:
  a confocal diaphragm unit;
  a splitting unit configured to spectrally spread the sample radiation into partial beams, the splitting unit being arranged downstream of the confocal diaphragm unit;
  a detector; and
  an imaging unit which images the partial beams on the detector in a spatially separated manner;
  wherein the confocal diaphragm unit is switchable between a confocal diaphragm with exactly m apertures for the sample radiation during illumination with m spots, and a confocal diaphragm with n apertures for the sample radiation during illumination with n spots; and wherein the splitting unit is switched between:
a first beam path for the sample radiation during illumination with m spots, the first beam path running from the confocal diaphragm unit to the imaging unit; and
a second beam path for the sample radiation during illumination with n spots, the second beam path running from the confocal diaphragm unit to the imaging unit.

\* \* \* \* \*